United States Patent [19]

Defaye et al.

[11] Patent Number: 4,739,043

[45] Date of Patent: Apr. 19, 1988

[54] METHOD FOR THE SYNTHESIS OF ALKYL, CYCLOALKYL OR ALCENYL ALDOSIDES OR POLYALDOSIDES

[75] Inventors: Jacques Defaye, Saint Ismier; Emile Wong, Grenoble; Christian Pedersen, Virum; Jean Chedin, Paris; Alain Bouchu, Villeurbanne, all of France

[73] Assignee: Beghin-Say, S.A., Thumeries, France

[21] Appl. No.: 860,195

[22] PCT Filed: Jul. 18, 1985

[86] PCT No.: PCT/FR85/00197

§ 371 Date: Apr. 18, 1986

§ 102(e) Date: Apr. 18, 1986

[87] PCT Pub. No.: WO86/00906

PCT Pub. Date: Feb. 13, 1986

[30] Foreign Application Priority Data

Jul. 19, 1984 [FR] France ................................ 84 11466

[51] Int. Cl.$^4$ .................... C07H 15/04; C07H 15/207; C07H 15/10

[52] U.S. Cl. .................................. 536/18.6; 536/18.4; 536/84; 536/111

[58] Field of Search ...................... 536/18.6, 18.4, 84, 536/111

[56] References Cited

U.S. PATENT DOCUMENTS

| | | | |
|---|---|---|---|
| 2,276,621 | 3/1942 | Langlois | 536/18.6 |
| 2,390,507 | 12/1945 | Cantor | 536/18.6 |
| 2,606,186 | 8/1952 | Dean et al. | 536/18.6 |
| 3,346,558 | 10/1967 | Roth | 536/18.6 |
| 3,375,243 | 3/1968 | Nevin et al. | 536/18.6 |
| 3,598,865 | 8/1971 | Lew | 536/18.6 |
| 3,928,318 | 12/1975 | Panusch et al. | 536/18.6 |
| 4,329,449 | 5/1982 | Roth et al. | 536/18.6 |

FOREIGN PATENT DOCUMENTS

EP106522 4/1984 European Pat. Off. ........... 536/18.6

OTHER PUBLICATIONS

Chemical Abstracts, vol. 9, No. 21, May 21, 1979, abstract 90:168854k.

Chemical Abstracts, vol. 85, No. 6, Aug. 9, 1976, abstract 85:34931z.

Carbohydrate Research, tome 110, 1982, Elsevier Scientific Publishing Company, (Amsterdam, NL), J. Defaye et al.: "The Behaviour of Cellulose, Amylose, and Beta-D-Nylon Towards Anhydrous Hydrogen Fluoride", pp. 217-227, especially pp. 217-219.

*Primary Examiner*—Ronald W. Griffin
*Attorney, Agent, or Firm*—A. W. Breiner

[57] ABSTRACT

The process comprises the action of a saturated aliphatic or cycloaliphatic alcohol or an aliphatic or cycloaliphatic alcohol comprising a double ethylenic bound not situated in alpha of the hydroxyl group with an aldose, aldoside or polyaldoside in the solvent and reactant formed by the hydrogen fluoride. Application to the synthesis of surfactants or as additives for rigidifying polyurethane foams.

16 Claims, No Drawings

METHOD FOR THE SYNTHESIS OF ALKYL, CYCLOALKYL OR ALCENYL ALDOSIDES OR POLYALDOSIDES

The subject of the invention is the provision of an improved method for the synthesis of alkyl, cycloalkyl or alcenyl aldosides or polyaldosides.

Alkyl aldosides and polyaldosides are well-known industrial products which can be used for a great variety of purposes and in particular as intermediates for obtaining surfactants or in the manufacture of polyurethane foams, for example.

STATE OF THE ART

It is known that alkyl aldosides or polyaldosides can be synthesized by reacting a hydroxylated compound with starch in the presence of an acid catalyst:

U.S. Pat. No. 2,276,621 describes the preparation of methyl-D-glucopyranosides by alcoholysis of starch in the presence of an acid catalyst such as sulfuric acid. In that case, the reaction is carried out at 100° C. for 2 hours in the presence of excess methanol in order to increase the yield of methyl glucosides.

U.S. Pat. No. 3,346,558 relates to the preparation of glucosides of polyols according to a continuous method. Thus ethylene glycol, glycerol, sorbitol glucosides are obtained by passing a mixture of starch, a polyalcohol and an acid catalyst such as paratoluene sulfonic acid or a Lewis acid like the etherate of boron trifluoride into an extruder heated to a temperature above 170° C.

U.S. Pat. No. 3,375,243 describes the preparation of alkyl glucosides and more particularly methyl-D-glucopyranosides from glucose or starch in the presence of excess methanol (3 moles per monosaccharide equivalent) and an acid catalyst such as paratoluene sulfonic acid (0.0025 to 0.1 mole per monosaccharide equivalent). The reaction is carried out in a reactor in a few minutes at a temperature between 100° and 250° C. under a maximum pressure of 15 to 20 bars. Under these conditions the methyl glucosides conversion rate is about 85 to 90%.

In U.S. Pat. No. 4,223,129, alkyl glucosides are prepared from starch and polyosides by a continuous method. The starch is suspended in alcohol in the presence of an acid inorganic or organic catalyst and passed under pressure into a coil having a well-delimited heating zone in which the reaction takes place. This apparatus is based on U.S. Pat. Nos. 2,735,792 and 3,617,383. In particular, in the preparation of methyl-D-pyranosides, the reaction temperature is of the order of 160° to 180° C., and the pressure adjusted in accordance with the desired contact time in the heating zone (8 to 20 minutes). The methanol/starch ratio may vary between 15:1 and 6.5:1 whereas the catalyst content is of the order of 0.005 per monosaccharide equivalent. Under these conditions, the methyl glucosides yield varies between 65 and 90%, mixed essentially with reversion di- and tri-saccharides. The authors indicate that this method is applicable to the preparation of $C_2$ to $C_{18}$ alcohol glucosides. Supplementing this method, U.S. Pat. No. 4,329,449 describes a method of crystallizing methyl-alpha-D-pyranoside, with recycling of the mother waters.

In the same field, U.S. Pat. No. 3,839,318 claims the preparation of alkyl glucoside by direct reaction under reduced pressure between glucose and an alcohol with heating in the presence of sulfuric acid under reduced pressure. The yields of alkyl glucosides vary under these conditions between 25 and 60%, the rest consisting of reversion alkyl oligosaccharides.

Another continuous method is described in Patent Application EP No. 96917. Alkyl glucosides ($C_8$ to $C_{15}$) are prepared by reacting an aldose, aldoside or polyaldoside with a 50% excess of alcohol in the presence of an acid catalyst, in particular toluene sulfonic acid, at a temperature between 80° and 150° C. Under these conditions, glucose is fed continuously, the water resulting from the reaction being removed as it is formed.

Other methods propose the utilization of ion-exchange resins.

Thus U.S. Pat. No. 2,606,186 describes the preparation of methyl glucoside by reacting glucose with methanol in the presence of an acid sulfonic resin. The reaction time is 1 to 48 h at a temperature of about 100° C. to avoid any degradation of the resin. The methyl glucosides crystallized after concentration of the nixture are separated by centrifuging.

Another method consists in the preparation of long chain alkyl glucosides by trans-glucosylation.

U.S. Pat. No. 3,219,655 describes the preparation of alkyl glucosides ($C_4$ to $C_{18}$) by trans-glucosylation in the presence of a sulfonic acid resin, it is shown that the method described by U.S. Pat. No. 2,606,186 is applicable only to the preparation of the methyl glucoside. Thus alkyl glucosides comprising more than 4 carbon atoms are prepared by transglucosylation from butyl glucoside, itself obtained from methyl-alpha-D-glucopyranoside. The preparation of alkyl glucosides according to this method is described also in DE Pat. No. 1905523 in which sulfuric acid is used as catalyst. The utilization of paratoluene sulfonic acid for the preparation of alkyl glucosides according to this method is recommended in EP Pat. No. 92875.

Treating a mixture of crude alkyl glucosides in a basic medium while heating is described in U.S. Pat. No. 3,450,690, it enables impurities to be removed and the crystallization of methyl glucoside to be facilitated. Likewise, treatment of a mixture of crude alkyl glucosides with a basic ion-exchange resin enables the colour of the mixture to be stabilized (U.S. Pat. No. 3,565,885).

It is moreover known from a publication *Carbohydr. Res.*, 110 (1982) 217, Defay et al., that dissolving polysaccharides (hexanes and pentosanes) like cellulose or xylene in hydrogen fluoride, results in the formation of oligosaccharides by fluorolysis.

SUBJECT OF INVENTION

The subject of the invention is the provision a new industrial method for obtaining alkyl, cycloalkyl or alcenyl aldosides or polyaldosides, with good yields.

The method is characterized in that a saturated aliphatic or cycloaliphatic alcohol or an aliphatic or cycloaliphatic alcohol including a double ethylene bond not situated in the alpha position of the hydroxyl group is reacted with an aldose, aldoside or polyaldoside in a solvent and reagent constituted by hydrogen fluoride.

The utilization of hydrogen fluoride as solvent and reagent gives access to alkyl-glycopyranosides from polyosides such as starch.

That in solution in hydrogen fluoride (HF), the starch solubilized in this solvent is converted principally into glucopyranosyl fluoride as well as several secondary compounds resulting from the auto-condensation of glucose. (reversion products).

The scheme below summarizes the presumed mechanism of the reaction which is the subject of the invention.

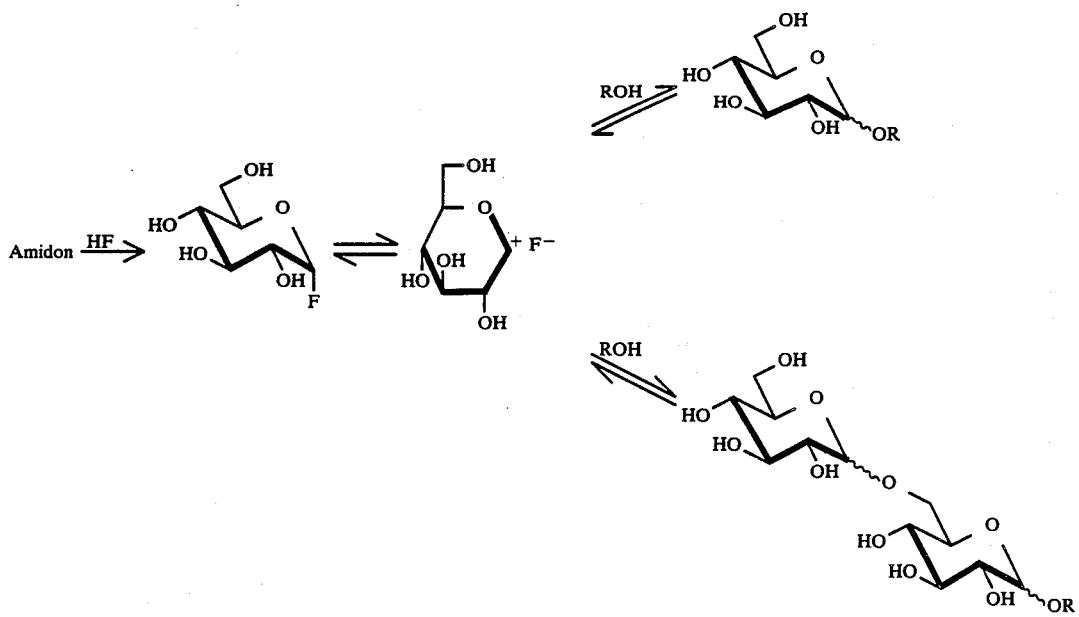

An intermediate glycosyl-oxycarbenium ion, stabilized by the fluoride ion, in equibrium with the glycopyranosyl fluoride has been postulated in this reaction to explain the rapidity of the hydrolysis observed as well as the formation of reversion products when the equilibrium is displaced by concentration of the solution (*Carbohydr., Res.*, 110 (1982) 217–227 (Diagram).

The addition of an alcohol to the reaction medium gives the corresponding glycoside, the existence of two anomers being explained by the intermediate oxy-carbenium ion and their proportion, by thermodynamic factors (Diagram). Alkyl-disaccharides, preferentially bonded (1→6) (Diagram), but also (1→2), (1→3), and (1→4) may be formed in this reaction under certain conditions. Some alkyl oligosaccharide glycosides in very minor proportions can also form according to the reaction scheme, under the conditions described in this patent.

The aim laid down was therefore to obtain alkyl glycosides with good yields from oses and polysaccharides using this reaction scheme.

The reaction is preferably carried out in a liquid medium. The temperature and pressure, contrary to those in the prior art, are not determinant conditions for this reaction, they condition principally the rate at which the reaction takes place. In favourable cases, preference is given to operating at ambient temperature or close to it, at atmospheric pressure, as this in fact is the easiest way. This temperature, which is not high, enables the percentage of by-products as well as the colour and the problems it raises to be reduced. But the reaction can be carried out at a lower temperature (up to $-25°$ C.). It can also be carried out at a higher temperature in the cases when this is recognised to be desirable, on condition of course that appropriate pressure and corrosion resistant equipment is used.

In addition, with this method there are no decomposition products of the furan type resulting from dehydration whereas these products are found with inorganic acids and acid resins.

Other advantages noted over prior methods relate to the possibility of recycling the reagents, the preferential formation of glucopyroranosealpha-D anomer with respect to the beta-D anomer and finally, the absence of partially hydrolysed products of the starting polysaccharides.

Alcohols that may be suitable are numerous and are chosen according to the final product it is desired to obtain.

As a non-limitative indication the following aliphatic or cycloaliphatic alcohols may be mentioned:

Primary alcohols of formula R-OH in which R is a $C_1$ to $C_{20}$ linear or branched group or a $C_4$ to $C_{20}$ alkyl group comprising at least one cycloalkyl group, or a $C_3$ to $C_{20}$ linear or branched alkyl group comprising an unsaturated ethylene bond not situated in the alpha position of the alcohol function.

Secondary or tertiary alcohols of formula R'-OH in which R' is a linear or branched $C_3$ to $C_{20}$ alkyl group or a $C_3$ to $C_{20}$ cycloalkyl or polyalkyl group or a linear or branched $C_4$ to $C_{20}$ alkyl group comprising an ethylene unsaturated bond not situated in the alpha position of the alcohol function.

Diols, triols and polyols, like ethylene glycol, glycerol, mannitol or sorbitol.

Amino alcohols like those of formula:

The name aldoses is given to monosaccharides which include an aldehyde function, like aldohexoses, aldopentoses, aldotetroses.

The name aldosides is given to compounds that result from ther acetalisation of an aldose with an alcohol either by the method according to the invention or any other known method, for example, one of those cited in the prior art. The reaction then takes place by an exchange of substitution groups.

The name alkyl-disaccharides (methyl . . . , ethyl . . . , etc . . . ) is given to oligosaccharide compounds which result from the glycosidation by the alcohol present in the reaction medium of di- or oligosaccharides that may result from the reaction, principally from disaccharides bonded (1→6) as shown in the previous scheme.

The name polyaldosides is given to oligo- and polysaccharides that result from the polymerization of the aldoses enumerated above, including disaccharides and trisaccharides. The polyaldosides are preferably chosen from plant polysaccharides. Starch and cellulose are the preferred polymers. Polysaccharides of animal or fungal origin (chitin, chitosan, etc.) are also suitable.

Among the aldoses, glucose is the preferred monosaccharide.

For the reaction to take place normally, an additional condition must be met, in particular in the case where polyaldosides are reacted: During the reaction between an aldose, aldoside or polyaldoside and hydrogen fluoride, oligosaccharide intermediates may be formed. If the quantity of alcohol is large, a high proportion of the oligosaccharides present in the medium will have a tendency to precipitate, which displaces the equilibrium of the mixture in solution towards the formation of oligomers. This process has tendency to slow down the reaction rate as additional time is required for the oligomers to be resolubilized. Thus, although the reaction is preferably carried out in excess alcohol with respect to the number of monosaccharide equivalents present it is desirable not to exceed an alcohol proportion (in mole)/monosaccharide equivalent of 60.

The name monosaccharide equivalents is given to the compounds that may result from the total hydrolysis of the polyaldosides reacted.

In addition, the quantity of hydrogen fluoride used in the reaction conditions the stability of the glucopyranosyl fluoride formed in the medium. Thus for an HF/monosaccharide eqivalent ratio of 90 the quantity of glucopyranosyl fluoride present in the final products is greater than 50%, despite the large excess of alcohol used, moreover the dissolution and fluorylisis of an aldose, aldoside or polyaldoside requires a minimum quantity of HF, an HF/monosaccharide equivalent proportion between 10 and 60 or better still, between 30 and 50 is therefore to be used preferentially.

Finally, it has been found preferable to use primary alcohols and preferably aliphatic alcohols, comprising at least 4 carbon atoms. For it seems that with higher alcohols protonation of the alcohol function hinders the course of the reaction.

The preferred alcohols are chosen from among methanol, ethanol, 1-propanol, 1-butanol, 3-butene-1-ol, allyl-alcohol.

A first variant consists in dissolving aldose, aldoside, or polyaldoside in hydrogen fluoride so as to cause the formation of the previously mentioned reaction intermediates. To the mixture is then added the alcohol in excess in proportions preferably 20 times greater and preferably 50 times less than the quantity in moles of aldoses, aldosides, or monosaccharide intermediates. The reaction is very rapid and gives the desired alkyl or cycloalkyl or alcenyl aldoside or polyaldoside.

However, this method requires the use of a large quantity of alcohol. It is for that reason that preference is given to the following variant which in addition offers the advantage of enabling the HF to be recovered, a crucial problem, and in addition the yield to be increased.

To a mixture of HF and alcohol and aldose, an aldoside or polyaldoside is added, preferably with stirring, and the resultant compounds then separated. Preferably, the aldose, aldoside or polyaldoside is added in a way such that an alcohol/monosaccharide equivalent proportion of between 3 and 20 moles or, still better, between 6 and 15 is obtained.

When a heavier alcohol is used, from $C_5$, a cosolvent facilitating the dissolution of this reagent in HF may be necessary; dioxan or sulfur dioxide are appropriate solvents in this case. These solvents moreover limit protonation of the alcohol.

The examples below illustrate the invention.

An analysis of the mixtures of methyl glucosides formed waw made by n.m.r. of $^{13}C$ and gas chromatography analysis of the acetylated and silylated derivatives according to one of the following methodologies:

acetylation by acetic anhydride in the presence of pyridine.

Silylation by a mixture of bis-trimethylsilyltrifluorylacetamide (BSTFA) and trimethylchlorosilane (TMCS).

Analysis on OV-1 capillary column.

The water content of the starches used was measured by the thermogravimetric balance method. In the examples that follow, it was, unless otherwise stated:

10% for wheat and maize starches

14% for potato starch.

It will be noted that the yields given in the examples are not optimized, they must be considered as minimum values under the operating conditions.

EXAMPLE 1

Synthesis of methyl-D-glucopyranosides by prior dissolution of the starch.

In a polyethylene vessel 10 g of maize starch (0.055 mole) were dissolved in 25 ml of hydrogen fluoride (1.25 mole) at 25° C. After 15 minutes stirring with a magnetic stirrer, 50 ml of methanol (1.25 mole) were added to the solution, that is, 23 monosaccharide equivalents, and the reaction mixture stirred for 45 minutes. The total reaction time was 1 hour. The reaction mixture was then precipitated in 300 ml of ethyl-ether with gentle magnetic stirring followed by filtration. Finally, the dried precipitate was filtered under reduced pressure in the presence of calcium carbonate.

The reaction yield with respect to the quantity of anhydrous starch used was 90%. 9.7 g of products were obtained in the following proportions:

| | |
|---|---|
| Methyl-D-glucopyranosides (alpha and beta) | 50% |
| Methyl-disaccharides (alpha and beta) | 50% |

A test was performed under the same conditions with 40 ml hydrogen fluoride (2 moles) and 100 ml methanol (2.5 moles), that is, 45 monosaccharide equivalents gave 10.2 g of products in the following proportion, the yield being 98%:

| | |
|---|---|
| Methyl-D-glucopyranosides (alpha and beta) | 80% |
| Methyl-disaccharides | 20% |

EXAMPLE 2

In this example therefore as well as in all the following examples alkyl glucoside was synthesized by means of a hydrogen fluoride-alcohol mixture.

To a mixture of hydrogen fluoride (2.5 moles) contained in a polyethylene flask, 10 g of maize starch were added at ambient temperature. The quantity of alcohol was therefore equal to 12.5 equivalents per monosaccharide equivalent. After rapid dissolution of the starch, the mixture was allowed to stand while being stirred with a magnetic stirrer.

The addition of 500 ml of ethyl-ether caused the precipitation of the reaction products formed, which were separated by filtration and washed with ether. They were dried under reduced pressure in the presence of calcium carbonate and gave 9.2 g of a light-beige syrupy compound whose analysis showed that it was composed of:

| Methyl-alpha-D-glucopyranoside | 80% |
|---|---|
| Methyl-beta-D-glucopyranoside | 10% |
| Methyl disaccharides | 10% |

The yield of methyl glucoside was 85% by weight with respect to the initial dry starch and it was noted that under these conditions, neither glucose nor glucopyranoside derivatives were found to be present.

EXAMPLE 3

Under the same operating conditions as in Example 2, but dividing the quantity of methanol by two, a larger quantity of methyl disaccharides was obtained (20%).

After treatment, analysis of the mixture of methylglucoside gave the following results:

| Products obtained 9.5 (yield 88%) | |
|---|---|
| Methyl-alpha-D-glucopyranoside | 70% |
| Methyl-beta-D-glucopyranoside | 10% |
| Methyl disaccharides | 20% |

This result showed that glucopyranoside fluoride reacts similarly with methanol and the primary hydroxyls of the glucose units and that the monosaccharide yield is a growing function of the molar ratio of alcohol/monosaccharide equivalents.

EXAMPLE 4

In this and the following examples, the tests were conducted in a manner such as to recover the residual hydrogen fluoride/alcohol mixture. They were carried out in a stainless steel reactor (316 Ti), capable of operating at a pressure of up to 18 bars, with magnetic stirring. Heating and cooling were provided by means of a jacket. In order to evaporate the HF/alcohol mixture on completion of the reaction, the reactor could be connected to a double-stage slide vane rotary vacuum pump, giving an average vacuum of 0.1 mm of mercury, the mixture was then recovered in a liquid nitrogen condenser. This indication of vacuum (0.1 mm of mercury) is not at all limitative.

10 g of maize starch (0.055 mole) were reacted with a mixture of 50 ml of hydrogen fluoride (2.5 moles) and 30 ml of methanol (0.75 mole). The reaction was carried out for 10 minutes at 40° C. The temperature was then reduced to 30° C. before evaporation. The excess HF-methanol mixture was evaporated under reduced pressure (0.1 mm Hg) in 20 minutes, 9.5 g of a pinkish-red, slightly acid syrupy compound were recovered (0.1% with respect to the HF used). The mixture was taken up with 20 ml of water and neutralized with calcium carbonate. The excess carbonate as well as the calcium fluoride formed were filtered and washed with cold water. The filtrate was then demineralized with a mixed ion-exchange resin and then concentrated while hot under reduced pressure.

Analysis of the colourless mixture finally obtained in the form of a powder gave the following results:

| Products recovered: 9.2 g | |
|---|---|
| Methyl-alpha-D-glucopyranoside | 65% |
| Methyl-beta-D-glucopyranoside | 25% |
| Methyl disaccharides | 10% |

This test showed that raising the temperature appreciably increases the reaction rate. The disaccharides content remains constant, heating influencing only the methyl glucoside alpha/beta anomers ratio.

EXAMPLE 5

Tests were carried out to examine the influence of the water introduced, for example, by the starch during recyclings of the HF/alcohol mixture. The tests were carried out on undried wheat starch from a well-defined HF/methanol mixture by adding increasing quantities of water directly into the HF.

At ambient temperature, the starch dissolution rate remained very rapid up to 0.4 equivalent H₂O/HF. Beyond this figure, dissolution slowed down. Under the test conditions of Example 4, 10 g of wheat starch were dissolved in 10 minutes in ambient temperature in a mixture of 50 ml HF, 30 ml methanol and 2.5 ml water, that is, 5% with respect to the HF. After 2 hours stirring, the HF/alcohol mixture was evaporated.

The presence of methyl-D-glucopyranosides mixed with the remainder of starch oligosaccharides (5%) was found to be present in the syrupy mixture obtained. Under the same conditions, heating for 30 minutes at 40° C. enabled complete fluorolysis and methanolysis of the starch to be obtained.

Analysis of the colourless product obtained gave the following results:

| Weight of crude product: 9 g | |
|---|---|
| Methyl-alpha-D-glucopyranoside | 60% |
| Methyl-beta-D-glucopyranoside | 25% |
| Methyl disaccharides | 14% |
| Glucose | 1% |

In addition, comparable results were obtained under the same conditions with water concentrations of up to 10% with respect to the HF used (equivalent to 5 or 6 to recyclings of the mixture if the starting starch contained 10% moisture), or water concentrations of up to 15% with respect to the HF used.

Under the evaporation conditions used, the mixture of crude products obtained contained 40 to 50% moisture provided by the starch representing 5% of total weight of the products formed.

EXAMPLE 6

Prior drying of the starch used would enable the HF/alcohol mixtures on completion of the reaction to be recovered more easily and efficiently.

Under the conditions of Example 4, 10 g of dried wheat starch containing 3% water (dried for 12 h at 50° C. under 50 mm Hg) were dissolved in 5 minutes at ambient temperature in a mixture of 50 ml of methanol.

After a reaction time of 1 hour, the HF/methanol mixture was evaporated. 10 g of a practically dry, syrupy compound, still slightly acid (0.1%/HF used) were recovered. Analysis of the product gave the following results:

| | |
|---|---|
| Methyl-alpha-D-glucopyranoside | 80% |
| Methyl-beta-D-glucopyranoside | 10% |
| Methyl disaccharides | 10% |

Taking up the whole of the mixture with hot methanol (20 ml) followed by cooling enabled the methyl-alpha-D-glucopyranoside to be crystallized out selectively.

In this example, the yield of methyl-alpha-D-glucopyranoside (containing 1 to 2% methyl-beta-D-glucopyranoside) was 60% after two successive crystallizations.

EXAMPLE 7

In order to reduce the quantities of reagent (HF, alcohol) with respect to the monosaccharide equivalents and limit the quantities of HF and alcohol to be evaporated, it was found that a reduction of the alcohol/monosaccharide equivalent ratio gave a much higher proportion of methyl disaccharides, as shown in the table below.

| | | | | | |
|---|---|---|---|---|---|
| Wheat starch in g | 10 | 20 | 20 | 30 | 40 |
| Water content % | 10 | 10 | 3 | 10 | 10 |
| HF, ml | 50 | 50 | 50 | 50 | 50 |
| Methanol, ml | 30 | 30 | 30 | 30 | 30 |
| Methanol/starch (mole/mole) | 13.6 | 6.8 | 6.8 | 4.5 | 3.4 |
| Reaction time, h | 1 | 1 | 1 | 1 | 1 |
| T en °C. | 40 | 40 | 40 | 40 | 40 |
| Methyl glucosides % | 90 | 85 | 85 | 75 | 65 |
| Methyl disaccharides % | 10 | 15 | 15 | 25 | 35 |

These tests were carried out at 40° C. as at that temperature it was found that the reaction was incomplete and unreacted oligosaccharide present, the conditions of the table from the second column beng moreover identical. In fact, increasing the temperature enabled the reaction rate to be increased when the quantity of starch was increased.

EXAMPLE 8

Under conditions similar to those for the synthesis of methyl glucoside, higher alcohol glucosides, up to $C_4$, can be obtained.

10 g of wheat starch (0.055 mole) were dissolved at ambient temperature in a mixture of 50 ml HF and 44 ml absolute ethanol (0.75 mole), that is, 13.6 equivalents per monosaccharide equivalent. The reaction was carried out in 1 hour 30 at ambient temperature. The HF/ethanol mixture was then evaporated in 40 minutes under reduced pressure (0.1 mm Hg) at 25° C. The residue was taken up with a minimum of water (20 ml) and neutralized with calcium carbonate. After filtration, the filtrate was passed through a mixed ion-exchange resin and concentrated to dryness.

Analysis of the product obtained gave the following results:

| Weight of crude product: 9.0 g | |
|---|---|
| Ethyl-alpha-D-glucopyranoside | 75% |
| Ethyl-beta-D-glucopyranoside | 10% |
| Ethyl disaccharides | 15% |

EXAMPLE 9

20 g of wheat starch were dissolved at ambient temperature in a mixture of 50 ml HF and 56 ml 1-propanol (6.8 equivalents per monosaccharide equivalent).

The reaction was carried out in 1 h at 40° C., with magnetic stirring. The HF/1-propanol mixture was evaporated in 30 minutes at 40° C. under 0.1 mm Hg.

After treatment as in Example 8 analysis of the mixture gave the following results:

| Products obtained: 18.1 g | |
|---|---|
| Propyl-alpha-D-glucopyranoside | 65% |
| Propyl-beta-D-glucopyranoside | 15% |
| Propyl disaccharides | 20% |

EXAMPLE 10

10 g of wheat starch were dissolved in a mixture of 50 ml HF (2.5 moles) and 7 g ethylene glycol (0.112 mole, that is, 2 molecular equivalents per monosaccharide equivalent) at ambient temperature, in the reactor. After 2 hours reaction at ambient temperature the HF was evaporated under reduced pressure in 20 minutes (without entrainment of glycol). The residue was taken up with 30 ml of water, neutralized with calcium carbonate and filtered.

The filtrate was concentrated by evaporation. The residual ethylene glycol was distilled by azeotropic entrainment with toluene. Analysis of the mixture recovered gave the following results:

| Weight of crude product: 9.4 g | |
|---|---|
| Glycol-mono-glucosides (alpha and beta) | 70% |
| Glycol-bis-glucosides | 20% |
| Glycol disaccharides | 10% |

Under the same conditions, an excess of ethylene glycol (0.22 mole–4 molecular equivalents) gave glycol-mono-glucoside with a yield of 85%, practically without any glycol-bis-glucoside (<5%).

EXAMPLE 11

10 g of wheat starch were dissolved in a mixture of 50 ml HF and 16 ml glycerol (0.22 mole), that is, 4 molecular equivalents, at ambient temperature.

The reaction was allowed to proceed for 2 h, with magnetic stirring at ambient temperature.

The HF was then evaporated under reduced pressure in 30 minutes. The mixture was taken up with 50 ml of water, neutralized with calcium carbonate and filtered; the filtrate was demineralized over mixed resin and then concentrated.

Analysis of the product obtained enabled a mixture of compounds with a glycerol/glucoside ratio of 7/3 and glycerol disaccharides, as well as unreacted glycerol to be found.

EXAMPLE 12

This direct oses and polyosides glycosidation in HF method gave reasonable yields with aliphatic alcohols comprising at the most 4 carbon atoms. With higher alcohols, protonation of the hydroxyl function observed by n.m.r. of $^{13}C$, probably hindered alkylation of the glycosyl-oxycarbenium ion. This disadvantage can be overcome by diluting the hydrogen fluoride with dioxan or sulfur dioxide. For it was observed, taking 1-octanol as example, that the protonated species of this alcohol diminished according to the dilution of the medium by these solvents. Thus, above a 4/1 (v/v) HF/dioxan ratio, the octanol was found not to be protonated. The utilization of an HF/dioxan/1-octanol mixture enabled octyl glucosides given in the following examples to be synthesized:

Preparation of octyl-glucosides using the 4:1 (v/v) HF/dioxan mixture

To a mixture of hydrogen fluoride (25 ml, 1.25 mole) and dioxan (6.25 ml), were added 5 g of starch (water content reduced to 10%), the solution was stirred for 15 minutes.

1-octanol (22 ml), 5 equivalents per monosaccharide equivalent were added to the reaction mixture and the solution obtained kept and stirred for 30 minutes. After evaporation of the reagents under reduced pressure (1 mm Hg) at ambient temperature (recovery of HF/dioxan), then at 50° C. (recovery of octanol), 7.3 g of a syrupy product were obtained. Analysis showed that it consisted of:

| | |
|---|---|
| Octyl-alpha-D-glucopyranoside | 55% |
| Octyl-beta-D-glucopyranoside | 5% |
| Octyl disaccharides | 25% |
| Glucopyranosyl fluoride | 15% |

The conversion rate into octyl glucosides, calculated with respect to the octanol, was 17%.

When the proportion of glucopyranosyl fluoride increased (case of reaction mixture comprising 1 to 2 equivalents of octanol/monosaccharide equivalents). The proportion of glycosyl fluoride could be reduced by dilution with dioxan. In fact, from a 2:1 HF/dioxan (by volume) dilution rate, the quantity of glucosyl fluoride was only a few percent. The utilization of an HF/dioxan mixture of about 2:1 (by volume) is recommended in the case where the number of octanol equivalents per monosaccharide equivalent is 1 to 2, as in the example below.

EXAMPLE 13

Preparation of octyl glucosides using a 2:1 (by volume) HF/dioxan mixture

The operating conditions were identical with those in the preceding example, but the proportions were as follows:

| | |
|---|---|
| Starch (water content 10%) | 5 g |
| HF | 25 ml |
| Dioxan | 12.5 ml |
| 1-octanol | 4.5 ml |

After evaporation of the reagents, 7.2 g of a syrupy product were obtained. Analysis showed that it consisted of:

| | |
|---|---|
| Octyl glucosides | 35% |
| Octyl disaccharides | 40% |
| Non-glucoside reversion products | 20% |
| Glucopyranosyl fluoride | 5% |

The conversion rate with respect to the octanol used was about 50%.

EXAMPLE 14

Preparation of lauryl glucosides using a 2:1 (by volume) HF/dioxan mixture.

To a mixture of hydrogen fluoride (50 ml, 2.5 miles) and dioxan (25 ml) were added 10 g of starch (potato starch, water content 13%). The solution was stirred for 15 minutes. 1-duodecanol (12 ml, 1 equivalent per monosaccharide equivalent) was added to the reaction mixture and the solution stirred for 20 minutes at ambient temperature. The mixture was raised to 35° C. for 20 minutes to evaporate the hydrogen fluoride at atmospheric pressure. The evaporation of the excess alcohol as well as of the dioxan under reduced pressure (0.1 mm Hg) gave a solid product (14.5 g). Analysis showed that it consisted of the following compounds:

| | |
|---|---|
| Lauryl-alpha-D-glucopyranoside | 25% |
| Lauryl-beta-D-glucopyranoside | 5% |
| Lauryl disaccharides | 10% |
| Glucose | 55% |
| Reversion products | |
| Glucopyranoside fluoride | <5% |

The lauryl glucoside conversion rate with respect to lauric alcohol was 35%.

What is claimed is:

1. A method for the synthesis of alkyl, cycloalkyl or alcenyl aldosides or polyaldosides characterized in that a saturated aliphatic or cycloaliphatic alcohol or an aliphatic or cycloaliphatic alcohol comprising an ethylene double bond not situated in the alpha position of the hydroxyl group are reacted with an aldose, or aldoside or a polyaldoside in hydrogen fluoride solvent, said materials including the hydrogen fluoride being present in an amount sufficient to react and form an alkyl, cycloalkyl or alcenyl aldoside or polyaldoside.

2. A synthetic method according to claim 1, characterized in that the alcohol is a primary alcohol.

3. A synthetic method according to claim 2, characterized in that the alcohol is chosen from among those comprising more than 4 carbon atoms.

4. A synthetic method according to claim 1, characterized in that the aldose is glucose.

5. A synthetic method according to claim 1, characterized in that the polyaldoside is chosen from plant saccharides, starch or cellulose.

6. A synthetic method according to claim 1, characterized in that the polyaldoside is chosen from among polysaccharides of animal or fungal origin.

7. A synthetic method according to claim 1, characterized in that the molar hydrogen fluoride/monosaccharide equivalent ratio is between 10 and 60.

8. A synthetic method according to claim 1, characterized in that the molar alcohol/monosaccharide equivalent ratio is less than or equal to 60.

9. A synthetic method according to claim 1, characterized in that the aldose, aldoside or polyaldoside is dissolved in hydrogen fluoride, followed by addition of the alcohol, the molar alcohol/monosaccharide ratio being less than 50.

10. A synthetic method according to claim 8, characterized in that to an HF/alcohol mixture is added an aldose, an aldoside or a polyaldoside, the molar alcohol/monosaccharide ratio being between 3 and 20.

11. A synthetic method according to claim 1, characterized in that the reaction is carried out in a liquid medium.

12. A synthetic method according to claim 1, characterized in that the quantity of water admitted with the reagents remain less than 15% of the quantity of hydrogen fluoride.

13. A synthetic method according to claim 1, characterized in that the alcohol is diol, triol or polyol.

14. A synthetic method according to claim 1, characterized in that the alcohol is an amino alcohol.

15. A synthetic method according to claim 1, in which the alcohol comprises at least five carbon atoms, characterized in that an appropriate cosolvent is added facilitating the dissolution of the alcohol in the hydrogen fluoride and reducing the protonation capacity of the medium.

16. A synthetic method according to claim 15, characterized in that the cosolvent is dioxan or sulfur dioxide.

* * * * *